US007697981B2

(12) United States Patent
Sen et al.

(10) Patent No.: US 7,697,981 B2
(45) Date of Patent: Apr. 13, 2010

(54) METHOD AND APPARATUS FOR USING AN ELECTROMAGNETIC FIELD IN CELLULAR TRANSPLANTATION

(75) Inventors: Luyi Sen, Stevenson Ranch, CA (US); Guanggen Cui, Stevenson Ranch, CA (US); Hillel Laks, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 1603 days.

(21) Appl. No.: 10/508,730

(22) PCT Filed: Mar. 24, 2003

(86) PCT No.: PCT/US03/09057

§ 371 (c)(1),
(2), (4) Date: Sep. 21, 2004

(87) PCT Pub. No.: WO03/082007

PCT Pub. Date: Oct. 9, 2003

(65) Prior Publication Data

US 2005/0119518 A1    Jun. 2, 2005

Related U.S. Application Data

(60) Provisional application No. 60/366,705, filed on Mar. 22, 2002.

(51) Int. Cl.
*A61N 1/00* (2006.01)
(52) U.S. Cl. .......................................................... 607/2
(58) Field of Classification Search ............... 600/9–15; 607/2, 115, 118, 129, 145, 148, 152
See application file for complete search history.

(56) References Cited

U.S. PATENT DOCUMENTS

| 4,699,147 | A | * | 10/1987 | Chilson et al. | ............... 600/374 |
| 5,213,113 | A | * | 5/1993 | Hlinsky | ...................... 607/152 |
| 5,255,678 | A | * | 10/1993 | Deslauriers et al. | ......... 600/375 |
| 5,509,924 | A | * | 4/1996 | Paspa et al. | ..................... 607/5 |

(Continued)

FOREIGN PATENT DOCUMENTS

EP    0 561 068 A2    9/1993

OTHER PUBLICATIONS

PCT International Search Report for PCT Application No. PCT/US03/09057, dated Dec. 15, 2003, 3 pages.

(Continued)

*Primary Examiner*—Samuel G Gilbert
(74) *Attorney, Agent, or Firm*—Fenwick & West LLP (57) ABSTRACT

An electromagnetic field is applied to transplanted cells during their transplantation culturing to achieve confluence and alignment of transplanted cells into damaged tissue and organs, therefore improving the synchronization of electrical and mechanical tissue or organ functions. The electromagnetic field may be applied by catheter based devices to a selected portion of tissue or to the entire surface of a hollow body cavity or organ, such as a heart chamber. The electromagnetic field is provided by an expansible net or array from a catheter or on an inflatable balloon or stent. The electromagnetic field is also provided by an implantable net or array of electrodes which may either be hardwired to a pulse generator or coupled by means of wireless or inductive transmission.

24 Claims, 10 Drawing Sheets

U.S. PATENT DOCUMENTS

| | | | |
|---|---|---|---|
| 5,873,849 | A | 2/1999 | Bernard |
| 6,043,066 | A | 3/2000 | Mangano et al. |
| 6,068,650 | A * | 5/2000 | Hofmann et al. ............... 607/2 |
| 6,326,177 | B1 * | 12/2001 | Schoenbach et al. ..... 435/173.7 |
| 6,654,636 | B1 | 11/2003 | Dev et al. |
| 2002/0010492 | A1 | 1/2002 | Donovan et al. |
| 2003/0170898 | A1 | 9/2003 | Gundersen et al. |
| 2003/0204206 | A1 * | 10/2003 | Padua et al. .................... 607/2 |

OTHER PUBLICATIONS

Atkins BZ, Hueman MT, Meuchel J, Hutcheson KA, Glower DD, Taylor DA. Cellular cardiomyoplasty improves diastolic properties of injured heart. J Surg Res. Aug. 1999;85 (2) :234-42.

Hagege AA, Menasche P. Cellular cardiomyoplasty: a new hope in heart failure? Heart. Nov. 2000;84 (5) :465-6.

Li RK, Jia ZQ, Weisel RD, Mickle DA, Zhang J, Mohabeer MK, Rao V, Ivanov J. Cardiomyocyte transplantation improves heart function. Ann Thorac Surg. Sep. 1996;62 (3) :654-60;.

Scorsin M, Hagege A, Vilquin JT, Fiszman M, Marotte F, Samuel JL, Rappaport L, Schwartz K, Menasche P. Comparison of the effects of fetal cardiomyocyte and skeletal myoblast transplantation on postinfarction left ventricular function. J Thorac Cardiovasc Surg. Jun. 2000;119 (6) :1169-75.

Supplementary European Search Report, European Application No. 03745586.2, Nov. 27, 2009, 4 pages.

* cited by examiner

Implantable wireless device for long-term application of electric-magnetic field to whole heart

FIG 4a

Implantable wireless device for long-term application of electric-magnetic field to a part of the heart

A. Neonatal cardiac myocyte culture

Without EMF                With. EMF

B. Connexin 43 protein expression level in neonatal cardiac myoyctes culture

Western blot

Sample No.     1    2    3    4    5    6

With EMF        without -EMF

Figure 6.

A. EMF effect on the Ca++ transient of neonatal cardiac myocytes in culture

Without EMF          With EMF

B. Electromagnetic field effect on the amplitude of cell motion in neonatal cardiac myocytes in culture

Figure 7.

Electromagnetic field stimulation promots the confluence between the old cell and newly seeded cell in culture Figure 8. Electromagnetic field control the direction of cell grow

METHOD AND APPARATUS FOR USING AN ELECTROMAGNETIC FIELD IN CELLULAR TRANSPLANTATION

RELATED APPLICATIONS

The present application is related to U.S. Provisional Patent Application Ser. No. 60/366,705, filed on Mar. 22, 2002, which is incorporated herein by reference and to which priority is claimed pursuant to 35 USC 119.

BACKGROUND OF THE INVENTION

1. Field of the Invention

The invention relates to the field of cellular transplantation in living organisms.

2. Description of the Prior Art

Transplantation of somatic cells to supply the function of a deficient organ has been studied for decades. This technology, however, has only been successfully performed for bone marrow in clinical practice. Recent studies in skeletal muscles for Duchenne muscular dystrophy, in the liver for a bridge to transplantation, in the pancreas for islets of Langerhans or in the brain have also shown some inconsistent results.

Cell transplantation in the heart, also called cellular cardiomyoplasty, was most intensely studied, since it may be become a useful tool for repairing injured heart tissue. Like skeletal muscle, transplantation of contractile cells is required for improving the function of the injured heart. Like brain cells, adult cardiac myocytes are terminally differentiated. Most strategies used to attempt to overcome this disadvantage involves transplanting cells which have the ability to multiply. Among all kinds of cells, cultured fetal cardiomyocytes, allogeneic fetal skeletal myoblasts, especially, cultured autologous myoblasts have been shown to have some functional benefits, such as decreased infarct size and increased ejection fraction by 20%-30%. However, the results are again inconsistent. Most recently, several human trials have been initiated in Europe and the first case has been performed in U.S.

The major problem addressed by this technique is that the arrangement of transplanted cells usually is disorganized. These transplanted cells are not able to align with the surrounding cells and are rarely shown to be histologically confluent with recipients' myocytes. Electrical and mechanical non-synchronization between transplanted cells and recipient's tissue remains the major limitation for efficacy in clinical application.

BRIEF SUMMARY OF THE INVENTION

The illustrated embodiment of the invention is directed to the concept and applicable methodology for using an electromagnetic field to improve the confluence, alignment and electrical and mechanical synchronization of transplanted cells in the heart, skeletal muscle and nerve. A newly designed electromagnetic device is used for cardiac myocyte, skeletal muscle cell and neuron cell transplantation in a hollow organ, such as the heart and vessel, or in tissue, such as skeletal muscle and nerve fibers. This invention contemplates both: 1) a method of applying an electromagnetic field for cell transplantation; and 2) a device for applying of an electromagnetic field for cell transplantation in heart.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The concept of the invention is to introduce a new strategy, namely the application of an electromagnetic field for achieving confluence and alignment of transplanted cells in damaged tissue and organs, therefore improving the synchronization of electrical and mechanical tissue or organ functions.

Our preliminary studies have shown that the arrangement of any cultured fetal or adult cardiac myocytes, smooth muscle cells and neuron cells grown in vitro are disorganized compared with those in native tissue. If a pulsed electromagnetic field is applied to the cells during their culture, all of the cells grow along with the direction of the electromagnetic field. A peak electrical field strength of 50 mV/cm to 5V/cm is effective to induce a preferred or oriented growth pattern of the cells. A low frequency pulse rate of 0.2 Hz to 20 Hz has been observed to be efficacious to orient growth patterns. However, it must be expressly understood that many different field strengths and pulse rates, or field patterns may be employed other than those depicted and described here without departing from the spirit and scope of the invention.

Figure 5:
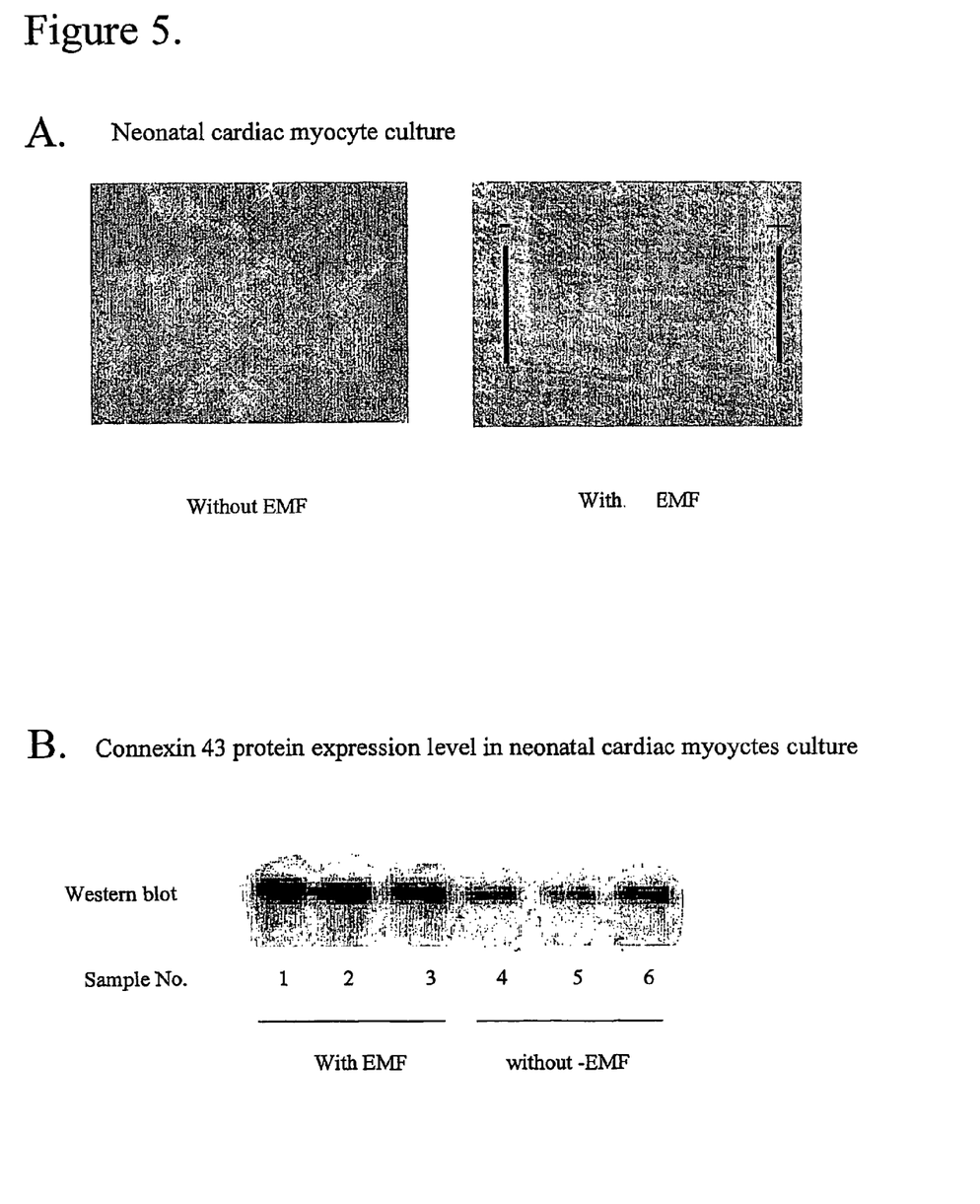
FIG. 5a is a pair of microphotographs, the left one of which shows a neonatal cardiac myocyte culture grown without EMF stimulation and the right one of which shows a neonatal cardiac myocyte culture grown with EMF stimulation.
FIG. 5b is a photograph of the measurement of connexin 43 protein in neonatal cardiac myocyte cultures grown with EMF in the case of samples 1-3 and without EMF stimulation in the case of samples 4-6.
Figure 6:
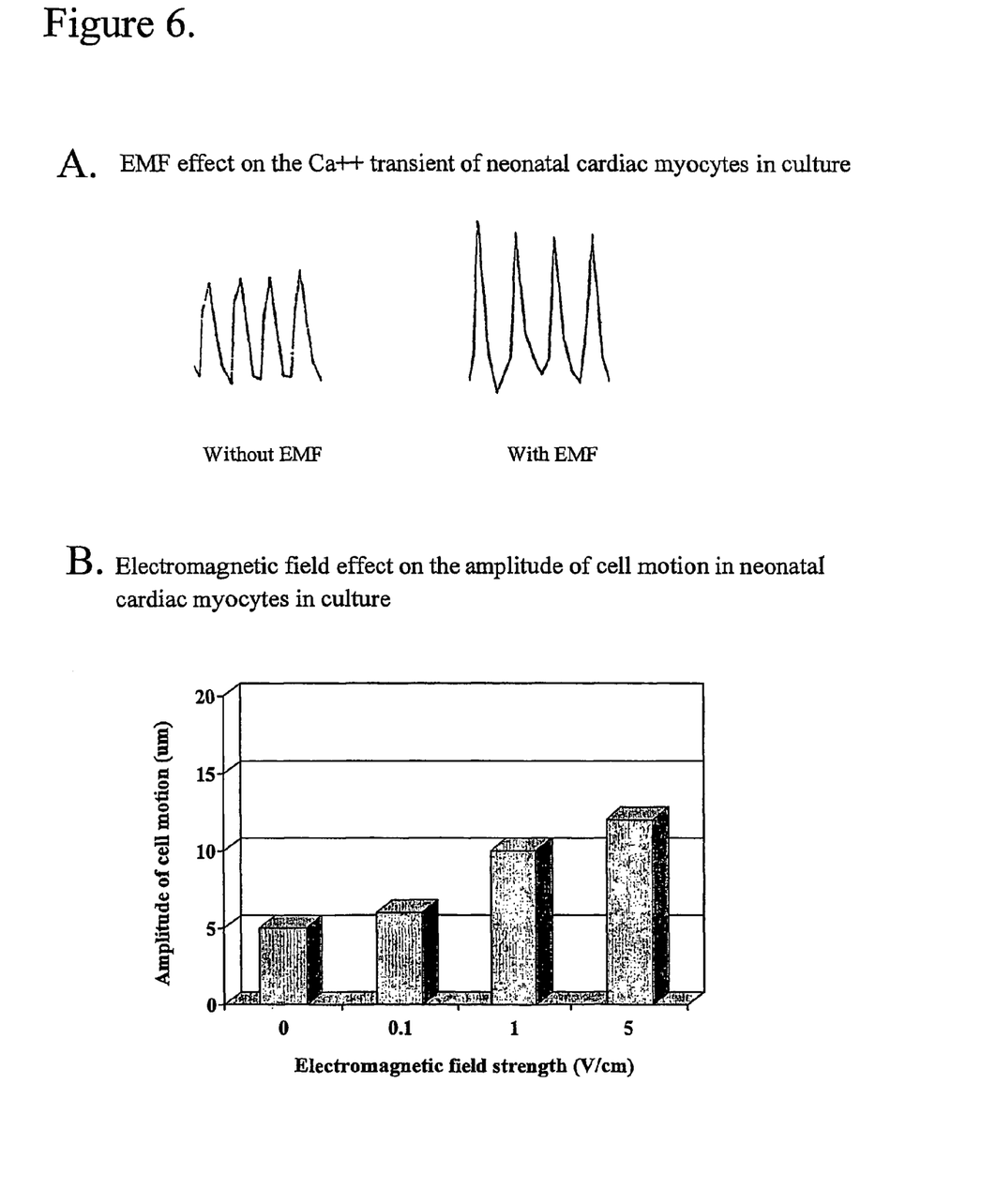
FIG. 6a shows segments of data showing the effect of EMF stimulation on the Ca++ transient in neonatal cardiac myocytes in culture. The data segment on the left is the Ca++ transient for cells grown without EMF stimulation, and the data segment on the right is the Ca++ transient for cells grown with EMF stimulation.
FIG. 6b is a bar graph showing the average amplitude of cell motion in μm as a function of electrical field strength to which the cells have been exposed during growth according to the invention.

Our preliminary data have shown that with an electromagnetic field stimulation (5 ms pulse, 1 Hz, 5 V/cm), the proliferation of cultured cardiac myocytes was significantly increased. The cell number in neonatal cardiac myocytes cultures was increased 3.5 fold compared with those without electric field stimulation as shown in the right side of microphotograph of FIG. 5a as compared to the left side respectively. The arrangement of the cells becomes organized. The gap-junction current is increased and the expression level of Connexin-43 is significantly increased as shown in EMF samples 1-3 on the left side of FIG. 5b as compared to the non-EMF samples 4-6 on the right side of FIG. 5b. Whole-cell Ca++ current as depicted in the graph of FIG. 6a, Ca++ transient and the amplitude of cell contraction are significantly increased as well. This phenomenon was observed in both neonatal and adult cardiac myocytes, smooth muscle cells and neuron ganglia cells. These observations suggest that an electric field is able to alter the arrangement of cultured electrically-excitable cells, and improve their alignment and confluence. The increase in cell motion as a function of the strength of the applied electrical stimulation during growth is depicted in the bar graph of FIG. 6b. There is a doubling of cell motion seen after the application of a field strength of 5 V/cm during growth.

Figure 7:
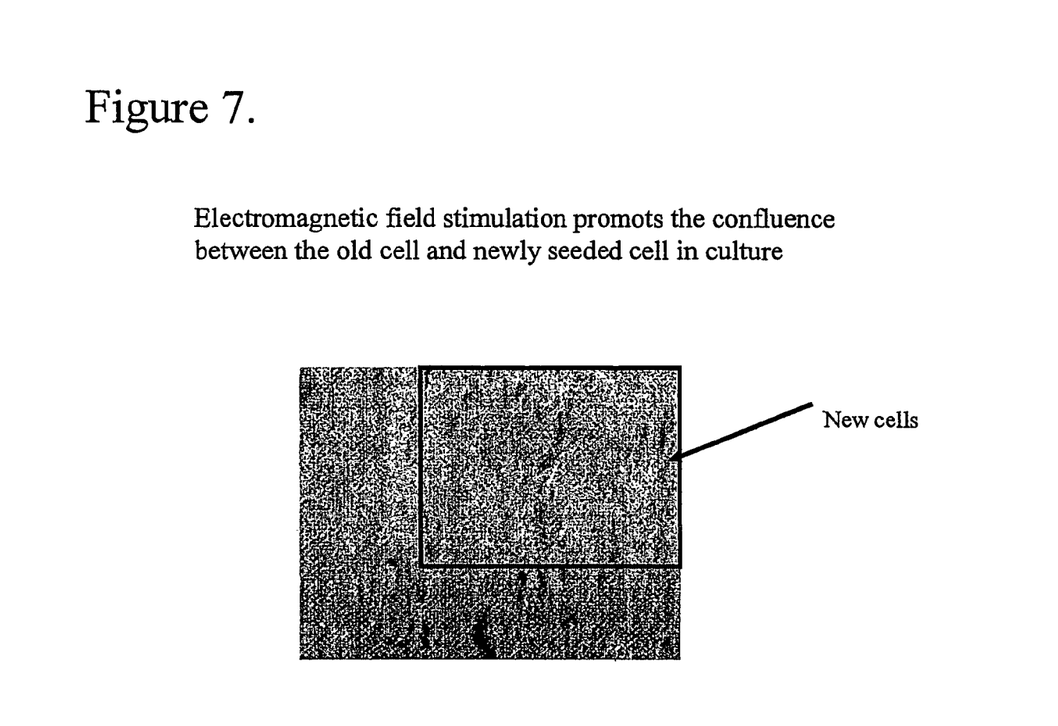
FIG. 7 is a microphotograph showing the confluence between old cell growth in culture and newly seeded cells in the culture when EMF stimulation according to the invention is applied during growth.

Moreover, seeding a second time in the same culture dish we found that the new cells grew in alignment with the old cells, growing confluently into the old cells while electric field is applied as depicted in the microphotograph of FIG. 7. The arrangement of these cells is organized in the same manner as in normal tissue. These cells can contract vigorously and synchronically.

Figure 8:
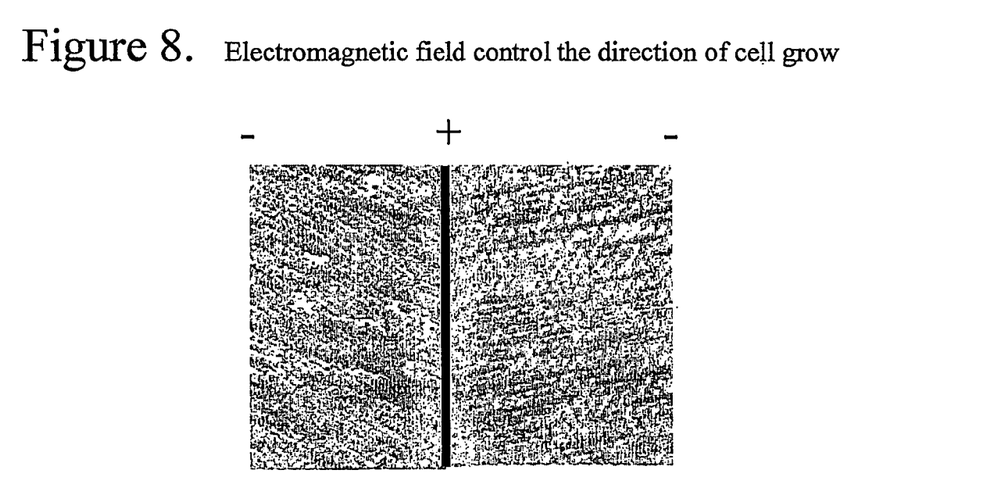
FIG. 8 is a microphotograph showing the change in orientation of cell growth in culture when the direction of the field of the applied electrical stimulation is changed or different on different sides of the anode, depicted by a solid line in the center of the microphotograph.

In our preliminary study, we also found that the long axis of the rod shaped myocytes always grow along the direction of the electromagnetic field fringe. Additionally, if we change the direction of the electromagnetic field, the direction of the growing cell will also change following the direction of the electromagnetic field fringe as depicted in the microphotograph of FIG. 8. These observations suggest that an electromagnetic field is able to control the direction in which these cells grow to allow us to generate a tissue with any cellular orientation needed. In view of the complexity of the myocardium structure, this feature could greatly improve the mechanical and electrical synchronization of the transplanted cells and surrounding tissue and reduce the coupling resistance.

In the illustrated embodiment of the invention the method is implemented into a method for cellular transplantation. After cells are transplanted into the target organ, an electromagnetic field with an optimized field strength and pulse frequency is applied to the transplanted area.

Figure 1A:
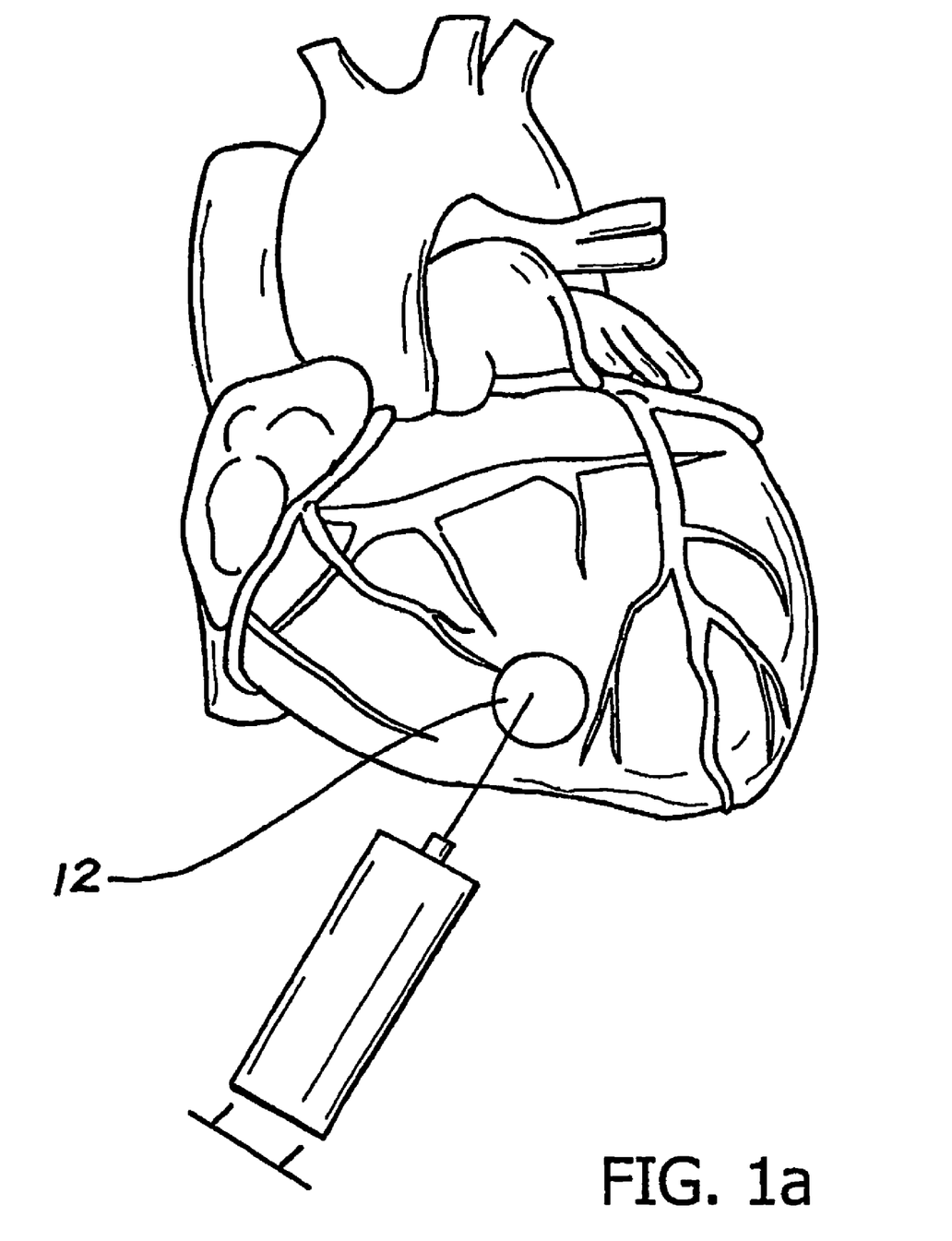
FIG. 1a is a side elevational view of a human heart showing the injection of transplanted cells into a chamber or target tissue area which has been identified by conventional means as damaged.
Figure 1B:
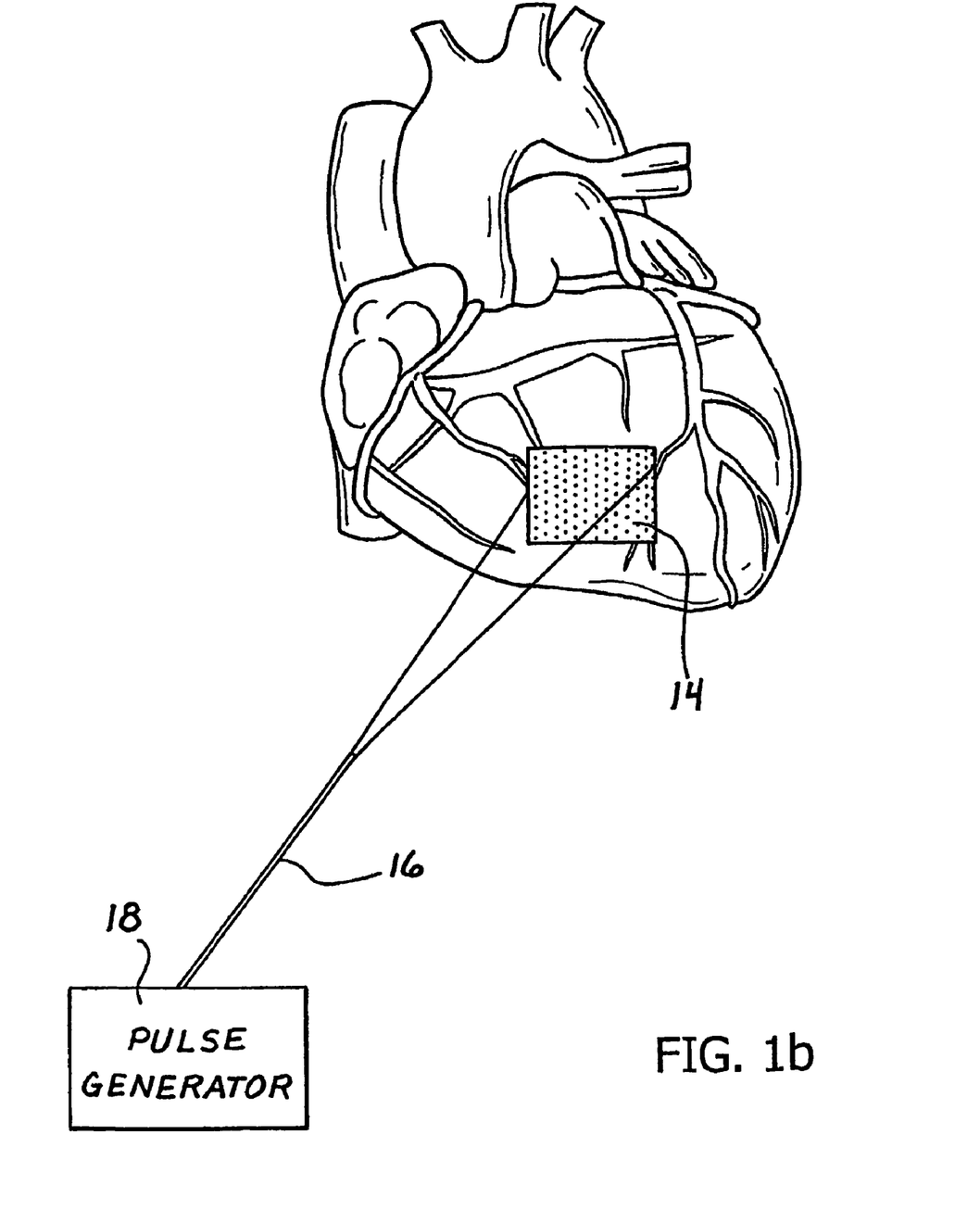
FIG. 1b is a side elevational view of a human heart of FIG. 1a showing the implantation or positioning of an electrode net or array coupled to a pulse generator for creating a predetermined electrical field during predetermined phases of cellular transplantation.

Consider three different designs for a device for applying an electromagnetic field in any organ or tissue. The first embodiment is illustrated in FIGS. 1a and 1b, which conceptually illustrate a noncatheter-based device for applying an electromagnetic field to transplanted cells directly from the outside of an organ, such as heart, pancreas, nerve, brain, skeletal muscle, etc. FIGS. 1a and 1b show a simplified side elevation view of a human heart 10. Cells are planted into a target area 12 by direct injection intra-arterial infusion into the target organ or tissue 12 during surgery. The electromagnetic field is applied using a non-catheter-based device. Typically, in post-infarction patients with a low ejection fraction, cellular transplantation into a damaged myocardium is performed during coronary artery bypass surgery. An electrode array 14 is directly placed on the transplanted area 12. A percutaneous wire 16 is connected to a pulse generator 18. The electric pulses are applied during the first week (or longer period of time) of post cellular transplantation.

Figure 2A:
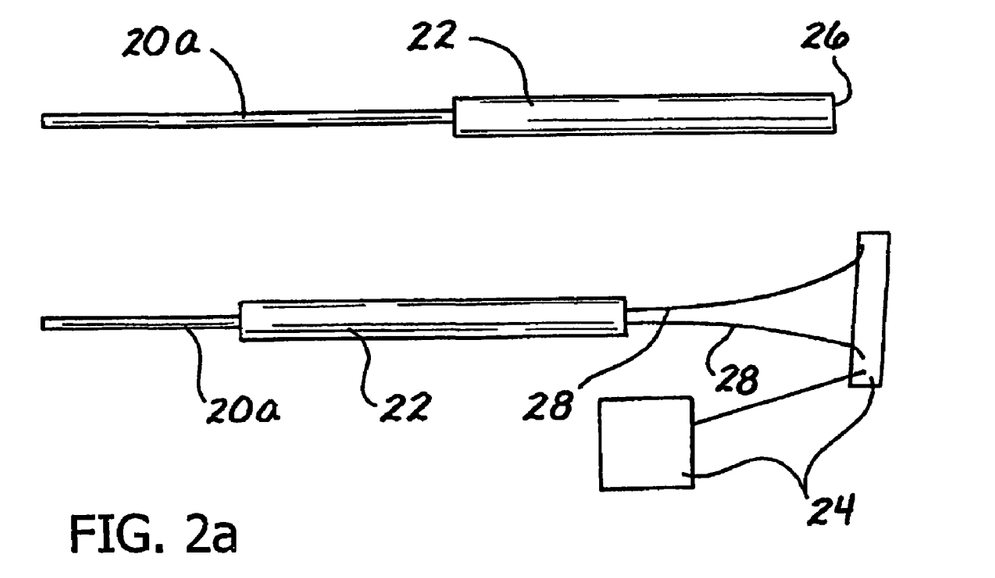
FIG. 2a illustrates a catheter-based means for providing electromagnetic manipulation of predetermined phases of cellular transplantation in a portion of target tissue after intracoronary injection of cells.
Figure 2B:
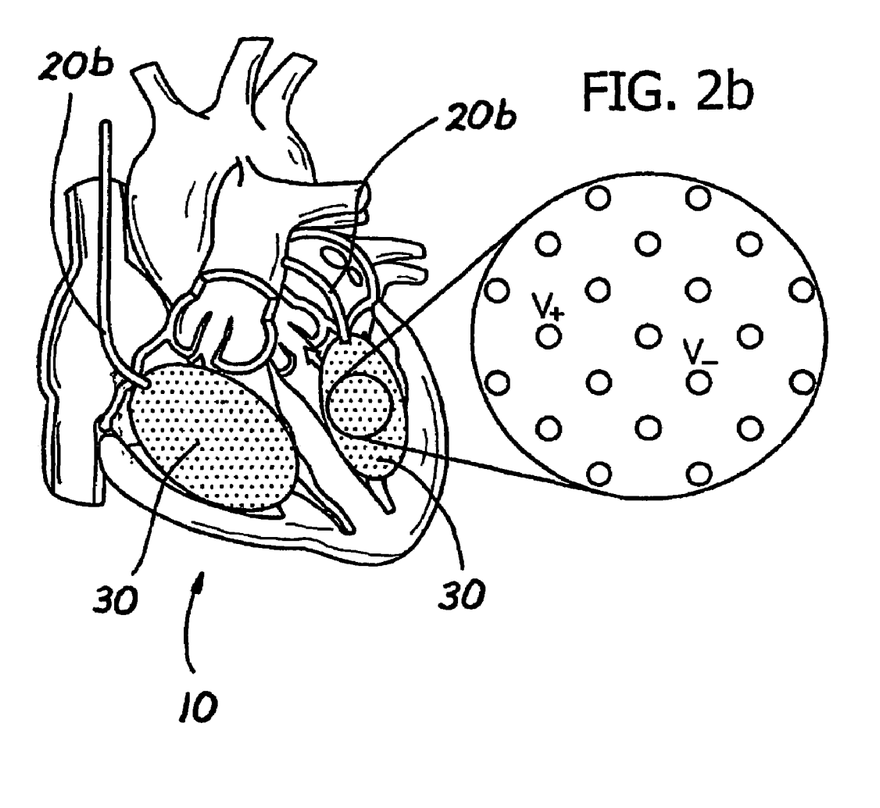
FIG. 2b illustrates a catheter-based means for providing electromagnetic manipulation of predetermined phases of cellular transplantation in a whole chamber of a hollow organ, such as a heart.

FIGS. 2a and 2b illustrate a catheter-based device for application of electromagnetic field to transplanted cells from the inside of an organ cavity, such as heart, vessel, etc. If the cells are transplanted by means of intra-arterial infusion, without surgically exposing the organs or tissue, the catheter-based device of FIGS. 2a and 2b is advantageously employed. In case of the heart, two kinds of catheters 20 are used for this purpose. One catheter 20b as shown in FIG. 2b is used for the whole cavity and the other catheter 20a as shown in FIG. 2a is used for a part or portion of the heart tissue. After the cells are infused through a coronary artery into the whole or part of the heart 10, catheter 20a or 20b is inserted into the heart cavity, usually either into the ventricle or atrium.

An array of electrodes is then deployed from catheter 20a or 20b to cover the interior or endocardial surface of the heart chamber or a portion of the endocardium. FIG. 2a shows catheter 20a which includes a protection sheath 22 on its distal portion. The displacement of sheath 22 relative to the distal end 26 of catheter 20a allows the expansible deployment of a net or resilient array 24 of interconnected electrodes. Net or resilient array 24 can be devised in any manner now known or later devised. In the illustrated embodiment array 24 is folded inside of sheath 22 and is stretched out or deployed in a predetermined three dimensional configuration or surface by means of the biased resiliency of a plurality of deployment wires 28, which may also carry the current to electrodes in net or array 24 from connectors (not shown) at the proximal end of catheter 20a. The form and mechanism by which expansible net or array 24 may be provided is not material to the invention. The technology of expansible stents and the like is readily available to provide a large variety of desired array shapes and qualities. Once deployed, net or array 24 is positioned against the target tissue area by manipulation of catheter 20a or anchored into the target tissue area by conventional means or anchors which are included as part of the structure of net or array 24.

In the case of a whole chamber deployment, net or array 24 is provided on the surface of an expansible balloon 30 as shown in FIG. 2b at or near the distal end of catheter 20b. Again wiring or conductive paths in catheter 20b provide for the electrically connection to the plurality of electrodes from on or in the exterior surface of balloon 30. The form and mechanism by which expansible net or array 24 may be provided on balloon 30 is again not material to the invention. The technology of balloon catheters is readily available to provide a large variety of desired array shapes and qualities for a balloon-supported and deployed net or array 24.

Figure 2C:
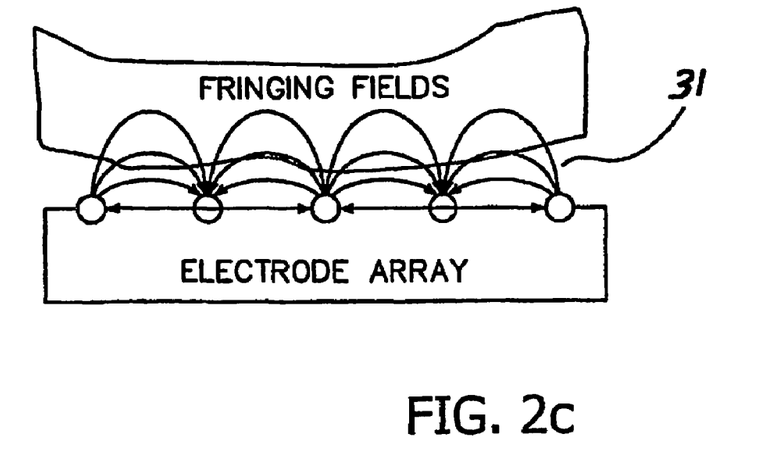
FIG. 2c is a simplified cross-sectional view in enlarged scale of the fringing electromagnetic field which is impressed into adjacent or proximal tissue by the electrode nets or arrays of the invention.

The catheter 20a or 20b is connected to a pulse generator 18 (not shown). The electric pulses are applied during the first week (or longer period of time) of post cellular transplantation. Fringing electromagnetic fields are formed between the electrodes in net or array 24 into the adjacent tissue as diagrammatically shown in FIG. 2c.

Figure 2D:
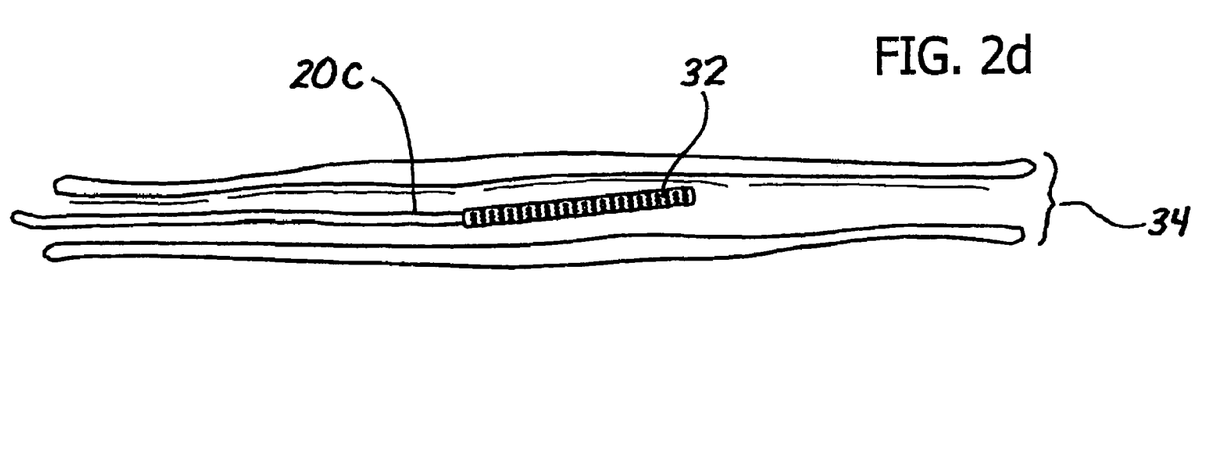
FIG. 2d illustrates a catheter-based means for providing electromagnetic manipulation of predetermined phases of cellular transplantation in an elongate hollow chamber, such as a vessel.
Figure 2E:
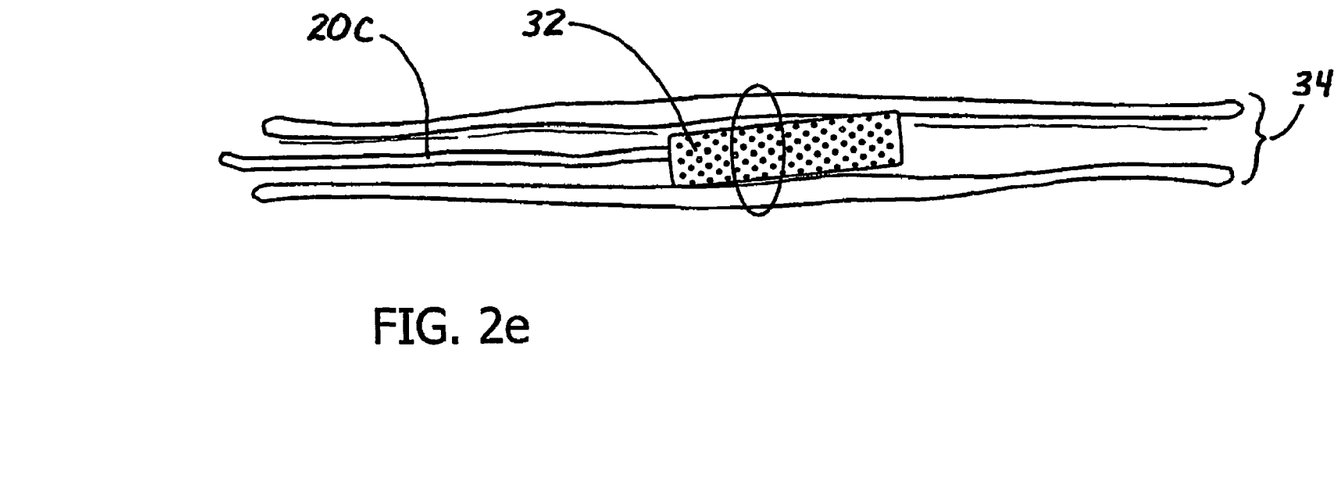
FIG. 2e is a simplified side view of the catheter-based means of FIG. 2d after the stent has been expanded in the vessel.
Figure 2F:
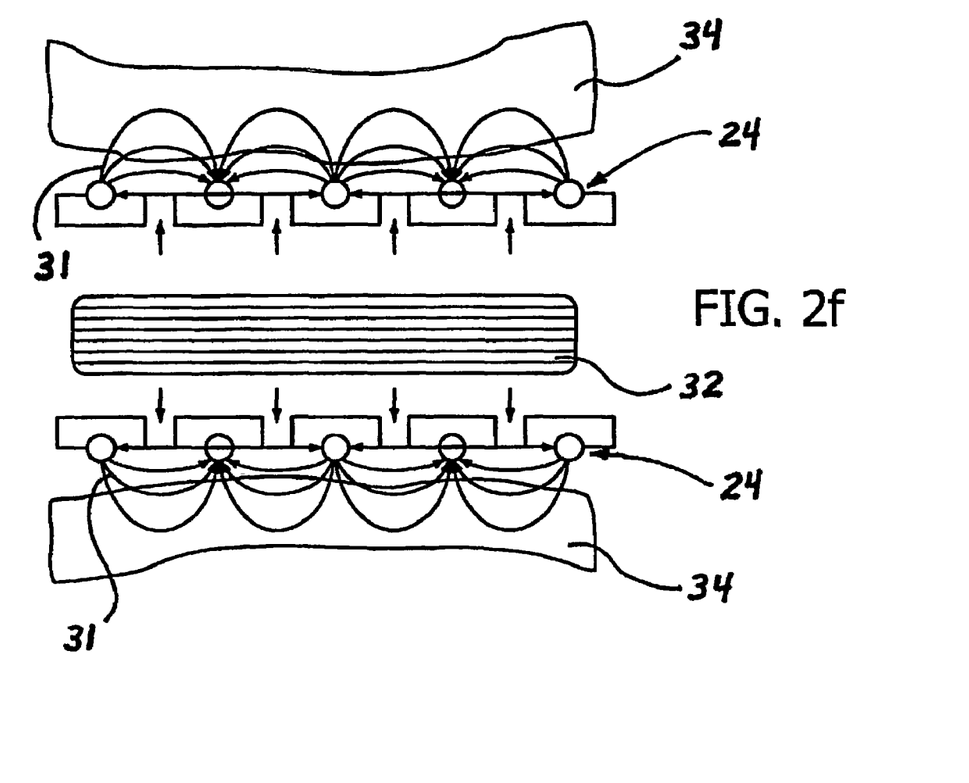
FIG. 2f is a simplified cross-sectional view in enlarged scale of the fringing electrical field which is impressed into adjacent or proximal tissue of the vessel by the electrode nets or arrays provided in the expansible stent.

FIGS. 2d, 2e and 2f illustrate a catheter based device used to promote cellular transplantation in a vessel or elongate hollow organ 34. In this embodiment a catheter 20c is provided with an expansible distal stent 32 on or in which the electrodes of net or array 24 are provided. FIG. 2f illustrates that after placement, stent 32 is expanded by conventional means thereby bringing net or array 24 in contact with or at least into close proximity to the interior walls of vessel 34. The electromagnetic field may then be applied and as shown in FIG. 2f the cellular infusion performed through the expanded supporting stent 32 thereby exposing the endovascular tissue of vessel 34 to the fringing fields of net or array 24.

Figure 3:
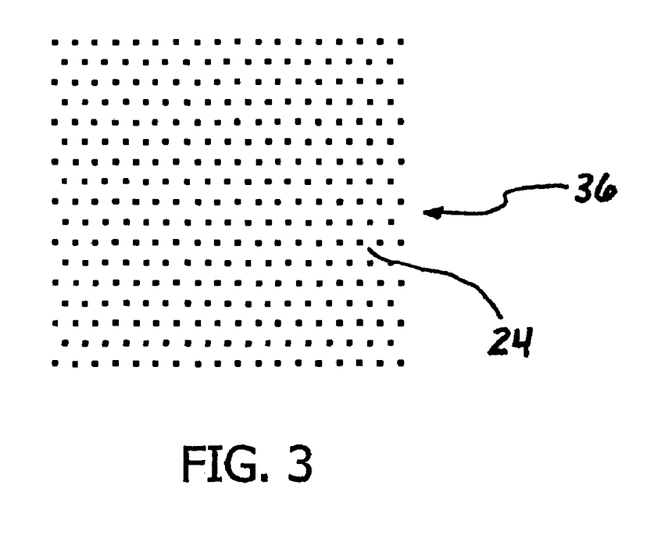
FIG. 3 is a simplified side view of a remotely powered, implanted net or array used to provide an oriented electromagnetic field during repeated or long term cellular transplantation, such as a receiving array implanted into a selected portion of a heart wall. This electrode array enables us to predetermine the orientation of transplanted cell growing with any angles or curves which will be coaligned in the direction of the surrounding tissue.
Figure 4A:
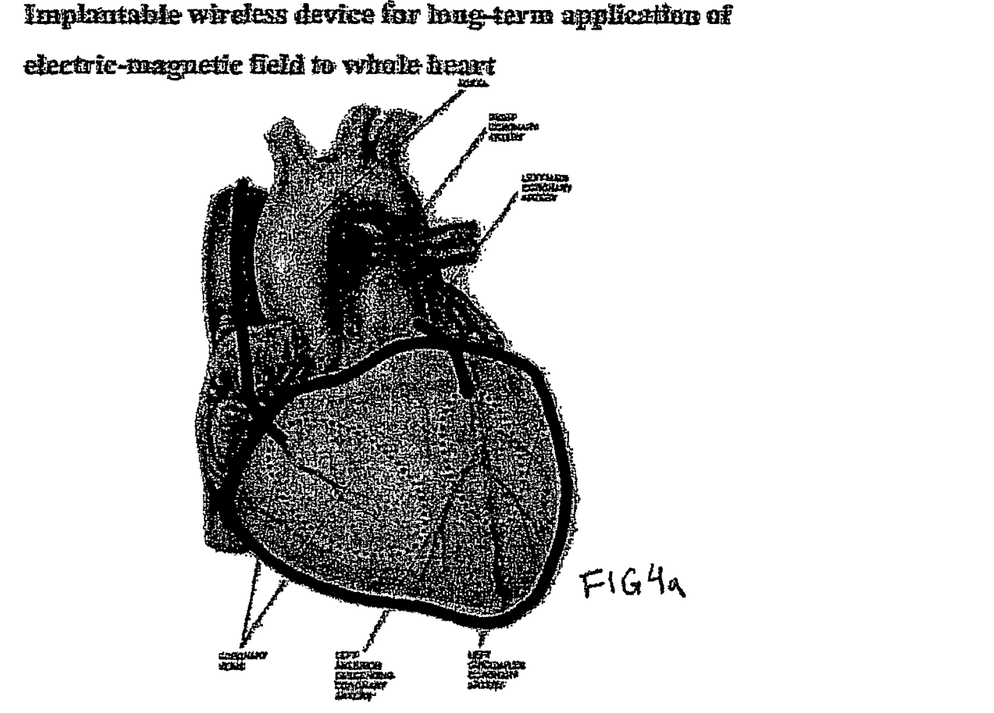
FIGS. 4a and 4b are diagrammatic depictions of devices and/or arrays implanted over, onto or into the heart in a whole-organ manner in FIG. 4a or relative to a selected region as shown in FIG. 4b.
Figure 4B:
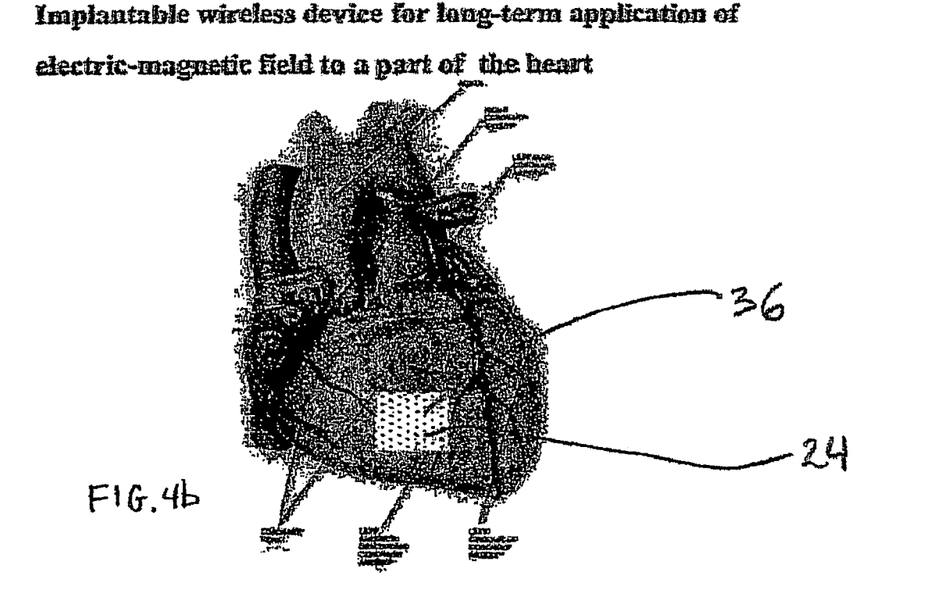

FIG. 3 illustrates an embodiment of the invention in which an implantable wireless device 36 which includes an array 24 is deployed for repeated or long-term application of an electromagnetic field to transplanted cells from the outside of an organ, such as heart, brain, or tissue, such as nerve, skeletal muscle, etc. The wireless device 36 is planted during the surgery, such as coronary artery bypass surgery as shown in FIGS. 4a and 4b. FIG. 4 diagrammatically illustrates a device 36 which is implanted over the exterior of the entire heart, while FIG. 4b diagrammatically illustrates a device 36 which is implanted into or onto only a selected region of the heart. The electric pulses are applied inductively by means of a broadcasting or inductive coupled pulse generator (not shown), which can be placed exterior to the chest cavity or subcutaneously implanted in the proximity of the heart. In this case, net or array 24 functions as a receiving antenna or inductor to the coupled electromagnetic energy from the coupled source or generator. The embodiment of FIG. 3 is used for long term therapy and repeated cellular transplantation procedure into a part or whole chamber of the heart. This embodiment thus avoids repeated catheter interventions and long-term catheterization induced infection and other complications.

The application of electromagnetic fields to the tissue facilitates and increases the efficiency of the cell transplantation. Using the devices described above, the target organ and tissue can electropermeablized. Electropermeablizaton allows the infused cells to penetrate the endothelia cell layer much easier and faster in catheter mediated cell transplantation. Specially, when biologically engineered cell transplantation to whole heart is performed in cardiomyopathy and heart failure patients, whole heart electropermeablizaton with low voltage high intensity pulses increases the efficiency of cell transplantation. It also facilitates cell transplantation by direct injection.

The invention overcomes a major obstacle and marks a new milestone in the cellular transplantation field. The invention opens a new era for biological study to explore the electromagnetic field effects on the biologic structure and function of the human and animal cells. This new technology, which has never been used in existing practices, however, has a potential to greatly improve the efficacy of the cell transplantation and make it to be clinically applicable.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for achieving confluence and alignment of transplanted cells in tissue comprising:
    transplanting cells into a selected region of the tissue;
    applying a pulsed electric field to the selected region of the tissue for a predetermined period of time, wherein applying the pulsed electric field comprises exposing the selected region of the tissue to a peak electrical field strength of approximately 50 mV/cm to 5 V/cm; and
    repeating application of a pulsed electric field to the selected region of the tissue with transplanted cells disposed therein.

2. The method of claim 1 where applying a pulsed electric field comprises exposing the selected region of the tissue to a pulsed electrical field with a pulse rate of approximately 0.2 Hz to 20 Hz.

3. The method of claim 1 where transplanting cells into a selected region of the tissue is repeated followed by repeated applications of the pulsed electric field to the selected region in which repeated transplantations occur.

4. The method of claim 1 where the repeated applications of the pulsed electric field occur over a period equal to or in excess of 24 hours.

5. The method of claim 1 where the repeated applications of the pulsed electric field occur over a period equal to or in excess of 7 days.

6. The method of claim 1, where the tissue is selected from a group consisting of: cardiac tissue, skeletal tissue, and nerve tissue.

7. The method of claim 1, where the transplanted cells are selected from a group consisting of adult cardiac myocytes, smooth muscle cells, neuron cells, autologous myoblasts, fetal cardiomyocytes, and allogenic fetal skeletal myoblasts.

8. The method of claim 1, where the tissue is located in a structure selected from a group consisting of: an organ, a vessel, a muscle, and a nerve fiber.

9. A method for achieving confluence and alignment of transplanted cells in tissue comprising the steps of:
    transplanting cells into a selected region of tissue; generating a pulsed electric field at the selected region of tissue; and
    applying the pulsed electric field to the transplanted cells in the selected region of tissue over a predetermined time, wherein applying the pulsed electric field comprises exposing the selected region of the tissue to a peak electrical field strength of approximately 50 mV/cm to 5 V/cm.

10. The method of claim 9 where the step of applying the pulsed electric field comprises applying the pulsed electric field by means of a noncatheter device for applying the pulsed electric field externally to a selected region of the tissue from an nonvascular position relative to the tissue.

11. The method of claim 10 where the step of applying the pulsed electric field comprises a step of applying the pulsed electric field to the selected region of tissue using an electrode array placed into contact with the tissue in which the transplanted cells have been transplanted.

12. The method of claim 9 where the step of generating the pulsed electric field comprises generating the pulsed electric field for a period of time after the cellular transplantation equal to or in excess of 24 hours.

13. The method of claim 9 where the step of generating the pulsed electric field comprises generating the pulsed electric field for a period of time after the cellular transplantation equal to or in excess of 7 days.

14. The method of claim 9 where the step of applying the pulsed electric field comprises applying the pulsed electric field to a selected region of the tissue from a vascular or internal position relative to the tissue by means of a catheter device.

15. The method of claim 14 where applying the pulsed electric field by means of a catheter device comprises deploying an electrode array from the catheter device to form an expansible net of electrodes coupled to a pulse generator for contact or near contact with the transplanted cells in the tissue.

16. The method of claim 14 where applying the pulsed electric field by means of a catheter device comprises deploying an electrode array on an expansible balloon, which is inflatable to substantially fill an organ cavity and thereby bring the electrode array into contact or near contact with the transplanted cells in the tissue.

17. The method of claim 9 where the step of generating the pulsed electric field comprises forming a fringing electric field between the electrodes of an array into the tissue.

18. The method of claim 17 where forming a fringing electric field between the electrodes of the array comprises providing an array of electrodes having an alternating pattern of electric polarity applied thereto by a pulse generator.

19. The method of claim 9 where the step of applying the pulsed electric field comprises forming a fringing electric field by means of an elongate cylindrical-shaped array of electrodes.

20. The method of claim 19 further comprising infusing the transplanted cells into the tissue through the elongate cylindrical-shaped array of electrodes.

21. The method of claim 9 where the step of generating the pulsed electric field comprises inductively powering an array of electrodes implanted into the tissue in proximity to the transplanted cells by inductively coupling a generator to the array.

22. The method of claim 9, where the tissue is selected from a group consisting of: cardiac tissue, skeletal tissue, and nerve tissue.

23. The method of claim 9, where the transplanted cells are selected from a group consisting of adult cardiac myocytes, smooth muscle cells, neuron cells, autologous myoblasts, fetal cardiomyocytes, and allogenic fetal skeletal myoblasts.

24. The method of claim 9, where the tissue is located in a structure selected from a group consisting of: an organ, a vessel, a muscle, and a nerve fiber.

* * * * *